(12) United States Patent
Fraley

(10) Patent No.: US 8,143,320 B2
(45) Date of Patent: *Mar. 27, 2012

(54) METHANOL PRODUCTION PROCESS AND SYSTEM

(75) Inventor: Lowell D. Fraley, Sugar Land, TX (US)

(73) Assignee: Starchem Technologies, Inc., Zurich (CH)

( * ) Notice: Subject to any disclaimer, the term of this patent is extended or adjusted under 35 U.S.C. 154(b) by 3 days.

This patent is subject to a terminal disclaimer.

(21) Appl. No.: 12/855,787

(22) Filed: Aug. 13, 2010

(65) Prior Publication Data

US 2011/0196049 A1 Aug. 11, 2011

(51) Int. Cl.
C07C 27/00 (2006.01)
(52) U.S. Cl. .................. 518/705; 518/700; 518/703
(58) Field of Classification Search .............. 518/700, 518/703, 705
See application file for complete search history.

(56) References Cited

U.S. PATENT DOCUMENTS

| | | |
|---|---|---|
| 2,514,294 A | 7/1950 | Rupp |
| 3,758,603 A | 9/1973 | Steigelmann et al. |
| 3,894,106 A | 7/1975 | Chang et al. |
| 3,934,412 A | 1/1976 | Masaki et al. |
| 3,979,472 A | 9/1976 | Butter |
| 3,998,898 A | 12/1976 | Chang et al. |
| 4,025,571 A | 5/1977 | Lago |
| 4,100,219 A | 7/1978 | Rodewald |
| 4,107,089 A | 8/1978 | Bondar et al. |
| 4,115,086 A | 9/1978 | Jordan et al. |
| 4,349,464 A | 9/1982 | Wainwright et al. |
| 4,368,695 A | 1/1983 | Davies |
| 4,404,414 A | 9/1983 | Penick |
| 4,499,327 A | 2/1985 | Kaiser |
| 4,545,895 A | 10/1985 | Brand et al. |
| 4,613,720 A | 9/1986 | Bonifaz et al. |
| 4,650,814 A | 3/1987 | Keller |
| 4,654,453 A | 3/1987 | Tabak |
| 4,698,452 A | 10/1987 | Le Van Mao et al. |
| 4,845,065 A | 7/1989 | Sugimori et al. |
| 5,026,935 A | 6/1991 | Leyshon et al. |
| 5,034,027 A | 7/1991 | Tien et al. |
| 5,043,522 A | 8/1991 | Leyshon et al. |
| 5,061,298 A | 10/1991 | Burgoyne, Jr et al. |
| 5,104,425 A | 4/1992 | Rao et al. |

(Continued)

FOREIGN PATENT DOCUMENTS

AU 2006270201 1/2007

(Continued)

OTHER PUBLICATIONS

Alternative Fuels and Chemicals from Synthesis Gas, Technical Progress Report No. 23, Apr.-Jun. 2000, prepared for the U.S. Department of Energy by Air Products and Chemicals, Inc., 5 pages.

(Continued)

*Primary Examiner* — Jafar Parsa
(74) *Attorney, Agent, or Firm* — Akin Gump Strauss Hauer & Feld LLP

(57) ABSTRACT

A process and a system are disclosed for producing methanol from synthesis gas. The synthesis gas is a stream containing $H_2$, CO, and $CO_2$ that is created using a nitrogen containing oxidant stream, such as air. The synthesis gas is then reacted through a conventional reactor system to create methanol. Unreacted synthesis gas is recycled back through the reactor system. The disclosed methanol production process can be mounted and operated on a seagoing vessel.

15 Claims, 4 Drawing Sheets

U.S. PATENT DOCUMENTS

| | | | |
|---|---|---|---|
| 5,173,513 A | 12/1992 | Pinto | |
| 5,177,114 A | 1/1993 | van Dijk et al. | |
| 5,215,648 A | 6/1993 | Zones et al. | |
| 5,424,335 A | 6/1995 | Abbott | |
| 5,430,211 A | 7/1995 | Pogue et al. | |
| 5,472,986 A | 12/1995 | van Dijk | |
| 5,491,273 A | 2/1996 | Santiesteban et al. | |
| 5,602,289 A | 2/1997 | van Dijk | |
| 5,811,621 A | 9/1998 | van Dijk | |
| 5,827,902 A | 10/1998 | Maretto et al. | |
| 6,191,175 B1 | 2/2001 | Haugaard et al. | |
| 6,303,839 B1 | 10/2001 | Marker | |
| 6,399,844 B1 | 6/2002 | van Dijk | |
| 6,433,239 B1 | 8/2002 | van Dijk | |
| 7,019,039 B1 | 3/2006 | Fraley | |
| 7,393,808 B2 | 7/2008 | Yoshida et al. | |
| 7,799,834 B2 | 9/2010 | Fraley | |
| 2003/0065042 A1 | 4/2003 | Shaw | |
| 2003/0096881 A1 | 5/2003 | Minkkinen et al. | |
| 2003/0236312 A1 | 12/2003 | O'Rear | |
| 2007/0208090 A1 | 9/2007 | van Dijk | |
| 2008/0318771 A1 | 12/2008 | Shimada et al. | |

FOREIGN PATENT DOCUMENTS

| | | |
|---|---|---|
| CA | 2303866 | 4/1999 |
| CA | 2571266 | 2/2006 |
| CA | 2613822 | 1/2007 |
| EP | 0060103 | 9/1982 |
| EP | 0359841 | 3/1990 |
| EP | 0839786 | 5/1998 |
| GB | 2237287 | 1/1991 |
| JP | HEI.10-508604 | 8/1998 |
| JP | 2004-315473 | 11/2004 |
| KR | 100912740 | 3/2008 |
| RU | 2198867 C2 | 2/2002 |
| WO | 93/06041 | 4/1993 |
| WO | 96/14279 | 5/1996 |
| WO | 99/15482 | 4/1999 |
| WO | 00/01643 | 1/2000 |
| WO | 01/47846 | 7/2001 |
| WO | 01/81280 | 11/2001 |
| WO | 03/078359 | 9/2003 |
| WO | 2006/012116 | 2/2006 |
| WO | 2006/126017 | 11/2006 |
| WO | 2007/011687 | 1/2007 |
| WO | 2007/142702 | 12/2007 |

OTHER PUBLICATIONS

European Supplementary Search Report, Aug. 31, 2010, 16 pages.
PCT Notification of Transmittal of the International Search Report and the Written Opinion of the International Searching Authority, or the Declaration (re: International Appln. No. PCT/US07/01549), Jul. 14, 2008, 8 pages.

Effect of A-stream Split          Sep/18/2006

| A split% | ATR outlet | | A-stream purge | | MEOH loop purge | | %Reactants in purges | | MEOH make |
|---|---|---|---|---|---|---|---|---|---|
| | H2 (lbmol/hr) | CO (lbmol/hr) | H2 (lbmol/hr) | CO (lbmol/hr) | H2 (lbmol/hr) | CO (lbmol/hr) | MEOH loop | A-stream | (lb/hr) |
| 0% | 71,905 | 28,115 | 0 | 0 | 2,516 | 2,987 | 14.9% | 29.6% | 997,948 |
| 10% | 71,905 | 28,115 | 1,458 | 214 | 3,729 | 2,101 | 14.5% | 29.6% | 987,831 |
| 20% | 71,905 | 28,115 | 2,915 | 428 | 3,253 | 1,468 | 15.3% | 29.6% | 971,849 |
| 30% | 71,905 | 28,115 | 4,373 | 642 | 4,769 | 961 | 19.5% | 29.6% | 942,306 |

Fig 4

METHANOL PRODUCTION PROCESS AND SYSTEM

CROSS-REFERENCE TO RELATED APPLICATIONS

This application claims priority to U.S. patent application Ser. No. 11/655,475 filed Jan. 19, 2007, which in turn claims priority to U.S. Provisional Application No. 60/809,260 filed May 30, 2006, both of these applications are incorporated herein in their entirety for all purposes.

BACKGROUND OF THE INVENTION

1. Field of the Invention

This invention relates to a process and system for production of methanol. More specifically, the invention includes a process and a system for producing methanol from combining a synthesis gas containing inerts, notably, nitrogen with a hydrogen-rich gas stream, and subsequently converting the hydrogen-rich synthesis gas stream to methanol, or other hydrocarbon chemicals. Even more specifically, the invention relates to such processes and systems capable of being mounted and operated on seagoing vessels, as well as on land.

2. Description of the Related Art

The evolution of methanol synthesis started at the beginning of the 20th century and reached commercialization in the mid 1920s. The reactants for methanol synthesis were $H_2$, CO, and $CO_2$, and this mixture was named "synthesis gas" or "syn gas." A stoichiometric mixture when passed through a catalyst bed, only reacted 12% of these reactants because the reaction was stopped by reaching equilibrium with the methanol generated by the reaction. The industry adopted the use of a recycle system, known as a "methanol loop," as a solution. The reacted gases from the catalyst bed were cooled, methanol condensed out, and the remaining gases re-circulated through the inlet to the catalyst bed. This system had the advantage of absorbing the exothermic heat generated at the catalyst site and carrying the heat to external heat exchangers. Up to 95% of the reactants were converted to methanol by this technique. This has been used in virtually all development of methanol synthesis during the last 80 years.

There are disadvantages of this system. The methanol loop placed a restriction on the purity of the syn gas. Consequently, inerts fed into the methanol loop with the syn gas had to be purged from the loop just after the methanol was condensed out. The purged inerts were intimately mixed with the valuable reactants, which were lost when purged along with the inerts. The prior art solution to this problem was to reduce the amount of inerts to as little as possible during syn gas preparation.

Modern practice in high capacity plants is to use an autothermal reformer ("ATR") to prepare the syn gas. The device mixes an oxygen containing gas stream with a natural gas stream to partially oxidize the natural gas in the top of the reformer vessel. The lower portion of the reformer vessel contains a catalyst, which brings the oxidized gases into chemical equilibrium. The major ingredient in natural gas is methane, which is converted to syn gas and $H_2O$.

Use of an ATR is also problematic because inerts are introduced into the natural gas stream along with the oxygen. To combat this problem, a cryogenic air separation ("C-ASU") was utilized to produce oxygen with the lowest possible inerts, generally between about 1% to 5%. The majority of the inerts were $N_2$ and Ar. Currently, there are no viable alternative processes for producing oxygen at large capacity and purity in this range. Cryogenic air separation is a difficult process to operate, has high maintenance and has a history of catastrophic explosions. Additionally, the $CH_4$ in the reformer vessel outlet acts as an inert in the methanol loop. Therefore, furnaces and reformers were operated at temperatures on the extreme upper limits of metal and ceramic materials to minimize the $CH_4$ remaining in the syn gas. For these reasons, the designs were expensive and consumed up to 80% of the overall plant energy.

Over the last 80 years, this approach has taken its toll in capital costs of the synthesis gas production portion of methanol plants.

| COST BREAKDOWN BY PLANT SECTION | |
|---|---|
| Syngas preparation | 60% |
| Methanol synthesis loop | 10 |
| Methanol distillation | 10 |
| Utilities | 20 |
| | 100% |

Prior art methanol production processes include those manufactured and sold by Lurgi AG of Frankfurt, Germany. Such prior art Lurgi systems have been disclosed, for example, in European Patent 0790226 B1, U.S. Pat. No. 5,631,302 and U.S. Pat. No. 5,827,901, which are hereby incorporated by reference in their entireties. Similar systems utilizing a methanol loop include those used by ICI and Holder-Topsoe, including those systems described in U.S. Pat. Nos. 6,387,963 6,881,759, 6,730,285, 6,191,175, 5,937,631 and 5,262,443, and United Kingdom Patent Nos.: 1,159,035 and 1,272,798, which are all hereby incorporated by reference in their entireties.

Synthesis gas has also been manufactured from oxidant streams high in nitrogen, such as air. Such processes have used separation processes, such as semi-permeable membrane technology, to separate air streams into high oxygen content streams and high nitrogen content streams. The high oxygen content streams were then reacted with natural gas to create synthesis gas, which was then converted to methanol.

Special reaction systems had to be developed because the high nitrogen content in the synthesis gas stream created problems in conventional methanol production processes by limiting the yield and the effectiveness of the methanol reactors. Such processes are disclosed in U.S. Pat. Nos. 5,472,986 and 7,019,039, which are hereby incorporated by reference in their entireties. These patents are assigned to Starchem Technologies, Inc. and the methanol production processes described therein are generally referred to herein as the "Starchem system." In the Starchem system, a reactor recycle stream (methanol loop) was not used because of problems associated with the high nitrogen content. As such, a series of single pass reactors were required.

Similarly, European Patent Application 0 261 771 proposed the use of air for production of a high nitrogen content synthesis gas which, thereafter, would be processed through a series of plug flow methanol reactors with interstage removal of methanol and water. As such, a series of single pass reactors were required, just as in the Starchem system.

The ATR and the methanol loop are not compatible without modifications. This can be explained in terms of the stoichiometric number ("$N_s$") defined as $N_s=(H_2-CO_2)/(CO+CO_2)$.

$N_s$ is commonly used as a measure of how syn gas will perform in the methanol loop. A number greater than 2 indicates an excess of hydrogen over that required for conversion of all the carbon to methanol. A number less than 2 indicates a hydrogen deficiency. The methanol loop may become inoperable when deficient in hydrogen. Make up gas ("MUG") is the name of the gas injected into the methanol loop. Experience has shown that a MUG with $N_s=2.05$ produces the most efficient and lowest capital cost methanol loop design.

A characteristic of an ATR is the reformed syngas has an $N_s$ of about 1.75. The traditional approach has been to add hydrogen to the effluent of the ATR to increase the $N_s$ of the MUG stream to about 2.05. The source of hydrogen has been from fired steam methane reforming or from refineries. More recently, the $N_s$ has been increased by rejecting $CO_2$ from the gas mixture as in Starchem's U.S. Pat. No. 7,019,039 for a series of single pass reactors.

It would be desirable to utilize prior art methanol production systems that include a methanol loop, with a synthesis gas produced through partial oxidation of natural gas using an air stream, such as the Starchem system. U.K. Patent Application 2,237,287A and Australian Patent AU-B-6459390 ("the AUS Process") describe the use of a synthesis gas formed from an oxygen enriched gas stream for the partial oxidation of natural gas and the use of a methanol loop reactor system for methanol production. In the AUS Process, a portion of the synthesis gas is not subject to the methanol synthesis loop. Rather, the synthesis gas is split into two distinct streams, stream "A" and stream "B," upon leaving the ATR. The "A" stream is diverted to a water gas shift reactor, converting CO to $H_2$, and then through a pressure swing absorber ("PSA") to extract the $H_2$. The $H_2$ that has been extracted joins the "B" stream and the combined flow is a hydrogen enhanced syn gas. This method is less than desirable because of the need for additional equipment for the extraction of the $H_2$ and the diversion of some of the synthesis gas, which results in a reduction in potential methanol production.

BRIEF DESCRIPTION OF THE DRAWINGS

These and other aspects, features, and advantages of the present invention will become apparent upon further consideration of the following detailed drawing figures, in which:

FIGS. 3 and 4 are a graph and table that illustrate the results of the comparative analysis of the AUS Process with the methanol production processes of the invention.

BRIEF SUMMARY OF THE INVENTION

Figure 1:
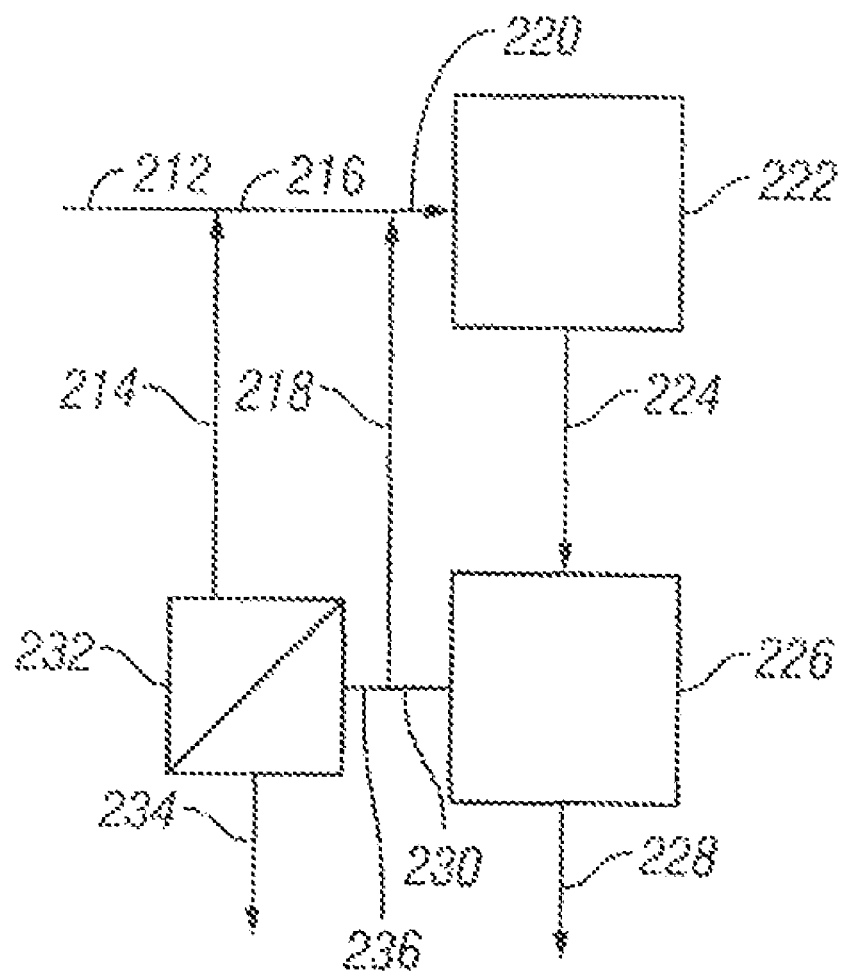
FIG. 1 shows an example of a simple process flow diagram in accordance with the present invention.

The present invention is a process and a system for creating methanol from synthesis gas. The synthesis gas is a stream containing $H_2$, CO, $N_2$ and $CO_2$, generated from a $N_2$ containing oxygen stream, such as air. The synthesis gas stream is reacted through a methanol loop system to create methanol. A specific embodiment of the present invention combines the Starchem system for creating synthesis gas, utilizing an air stream with the conventional methanol loop system for reacting synthesis gas to create a methanol stream, while avoiding prior art concerns of efficiency and methanol yield resulting from the presence of nitrogen in the system. Another specific embodiment of the present invention is a methanol production process such as described herein, which can be mounted and operated on a seagoing vessel, as well as on land.

In one aspect, the invention provides a process for producing methanol, comprising the steps of providing a synthesis gas stream comprising $H_2$, CO, and $CO_2$, and $N_2$, wherein the synthesis gas stream comprises at least about 6 mole % $N_2$ and wherein the synthesis gas stream comprises $H_2$, CO, and $CO_2$ in a ratio of $(H_2-CO_2)/(CO_2+CO)$, which is less than about 1.80. The synthesis gas stream is then combined with a hydrogen-rich gas stream to form a makeup gas stream, which is then combined with a recycle gas stream to produce a reactor feed stream. The reactor feed stream is introduced into a reactor system containing a methanol conversion catalyst, wherein a portion of the reactor feed stream is converted to methanol. A reacted gas stream is withdrawn from the reactor system and the reacted gas stream is separated into a crude methanol product stream and a gas stream. The gas stream is split into a recycle gas stream and a purge gas stream. The recycle gas stream is mixed with the makeup gas stream to form the reactor feed stream. The purge gas stream is then separated into a fuel gas stream comprising $CH_4$ and $N_2$ and a hydrogen-rich stream comprising $H_2$, and the hydrogen-rich stream is mixed into the synthesis gas stream.

In another aspect of the invention, a similar process for converting a natural gas to methanol is provided. The process includes providing an air stream having an oxygen content less than about 22% and enhancing the oxygen content of the air stream to between about 28% and 94% oxygen, thereby creating an enhanced oxygen stream. A natural gas stream comprising methane is then provided and the natural gas stream is partially oxidized in an autothermal reformer using the enhanced oxygen stream to create a synthesis gas stream comprising $H_2$, CO, and $CO_2$ and $N_2$. The synthesis gas stream is then combined with a hydrogen-rich gas stream to form a makeup gas stream, wherein the synthesis gas stream composition remains substantially unchanged after exiting the autothermal reformer until combined with the hydrogen-rich gas stream. The makeup gas stream is combined with a recycle gas stream to produce a reactor feed stream, which is introduced into a reactor system containing a methanol conversion catalyst; wherein a portion of the reactor feed stream is converted to methanol. A reacted gas stream is then withdrawn from the reactor system and separated into a crude methanol product stream and a gas stream. The gas stream is split into a recycle gas stream and a purge gas stream. The recycle gas stream is combined with the makeup gas stream to form the reactor feed stream. The purge gas stream is separated into a fuel gas stream comprising $CH_4$ and $N_2$ and a hydrogen-rich stream comprising $H_2$, and the hydrogen-rich stream is mixed into the synthesis gas stream.

In yet another aspect of the invention, a process is provided for producing methanol that comprises the steps of providing an air stream having an oxygen content less than about 22% and enhancing the oxygen content of the air stream to between about 28% and 94% oxygen, thereby creating an enhanced oxygen stream. A natural gas stream is provided that comprises methane. The natural gas is partially oxidized in an autothermal reformer using the enhanced oxygen stream to create a synthesis gas stream comprising $H_2$, CO, and $CO_2$, and $N_2$. At least about 90% of the synthesis gas stream is then combined with a hydrogen-rich gas stream to form a makeup gas stream, which is combined with a recycle gas stream to produce a reactor feed stream. The reactor feed stream is introduced into a reactor system containing a methanol conversion catalyst, wherein a portion of the reactor feed stream is converted to methanol. A reacted gas stream is withdrawn from the reactor system, which is separated into a crude methanol product stream and a gas stream. The gas stream is split into a recycle gas stream and a purge gas stream. The recycle gas stream is then mixed with the makeup gas stream to form the reactor feed stream. The purge gas stream is separated into a fuel gas stream comprising $CH_4$ and $N_2$ and a hydrogen-rich stream comprising $H_2$, and the hydrogen-rich stream is mixed into the synthesis gas stream.

In a further aspect of the invention, a process is provided for producing methanol, which comprises the steps of providing a synthesis gas stream comprising $H_2$, CO, and $CO_2$ and $N_2$, wherein the synthesis gas stream comprises at least about 16 mole % $N_2$ and wherein the synthesis gas stream comprises $H_2$, CO, and $CO_2$ in a ratio of $(H_2-CO_2)/(CO_2+CO)$ of about 1.73. The synthesis gas stream is combined with a hydrogen-rich gas stream to form a makeup gas stream, which is combined with a recycle gas stream to produce a reactor feed stream. The reactor feed stream is then introduced into a reactor system containing a methanol conversion catalyst, wherein a portion of the reactor feed stream is converted to methanol. A reacted gas stream is withdrawn from the reactor system and separated into a crude methanol product stream and a gas stream. The gas stream is then split into a recycle gas stream and a purge gas stream. The recycle gas stream is mixed with the makeup gas stream to form the reactor feed stream. The purge gas stream is separated into a fuel gas stream comprising $CH_4$ and $N_2$ and a hydrogen-rich stream comprising $H_2$, and the hydrogen-rich stream is mixed into the synthesis gas stream.

DETAILED DESCRIPTION OF THE INVENTION

In the present invention, the Starchem system for creating synthesis gas from the oxidation of natural gas using an air or other oxygen-containing stream is combined with a traditional methanol loop system. The present invention overcomes prior art concerns of using nitrogen containing synthesis gas in the traditional methanol loop system.

Starchem systems such as those disclosed in U.S. Pat. No. 5,472,986 and U.S. Pat. No. 7,019,039 B1 ("Starchem Patents") include processes for creating synthesis gas using an air stream, or other oxygen and nitrogen containing stream, separating the air stream into high oxygen and low oxygen content streams, and utilizing the high oxygen content stream in a partial oxidation reaction with natural gas to create a synthesis gas containing $H_2$, CO and $CO_2$. The Starchem Patents are incorporated herein by reference in their entirety for all purposes.

FIG. 1 discloses the present invention in a simple form. Synthesis gas stream 212, which contains at least about 6 mole % nitrogen, is combined with a hydrogen-rich gas stream 214 to form a make up gas ("MUG") stream 216, which has a stoichiometric number greater than 2.05. $N_s$ is used as a measure of how the syn gas will perform in the methanol loop. As such, it is commonly treated as a property of the syn gas. A number greater than 2 indicates excess hydrogen and a number less than 2 indicates a hydrogen deficiency. Excess hydrogen in the methanol loop increases the reaction rate and concurrently reduces the rate of formation of byproducts. It should be noted, however, that the synthesis gas stream may be produced by any means in accordance with the invention.

In a specific embodiment of the invention, the synthesis gas stream 212 contains at least about 8 mole % nitrogen. In another specific embodiment of the invention, the synthesis gas stream 212 contains at least about 20 mole % nitrogen. In a more specific embodiment of the invention, the synthesis gas stream 212 contains at least about 35 mole % nitrogen.

The makeup gas stream 216 is further combined with a recycle gas stream 218 to produce a reactor feed stream 220. Feed stream 220 is introduced into reactor vessel 222, which contains a methanol conversion catalyst.

A portion of the reactor feed stream 220 is then converted into methanol. The reacted gas stream containing methanol 224 is withdrawn from the reactor system and separated into a crude liquid methanol product stream 228 and gas stream 230. The gas stream 230 is then split into two streams, the first stream being the recycle gas stream 218, which is combined with the makeup gas stream 216 to form the reactor feed stream 220. The second portion is a purge gas stream 236. The purge gas stream 236 is separated into two streams, the fuel gas stream 234, which contains $CH_4$, CO, and $CO_2$ and $N_2$, and a hydrogen-rich gas stream 214. The hydrogen-rich gas stream 214 is then mixed into the synthesis gas stream 212 to form the makeup gas stream 216.

Figure 2:
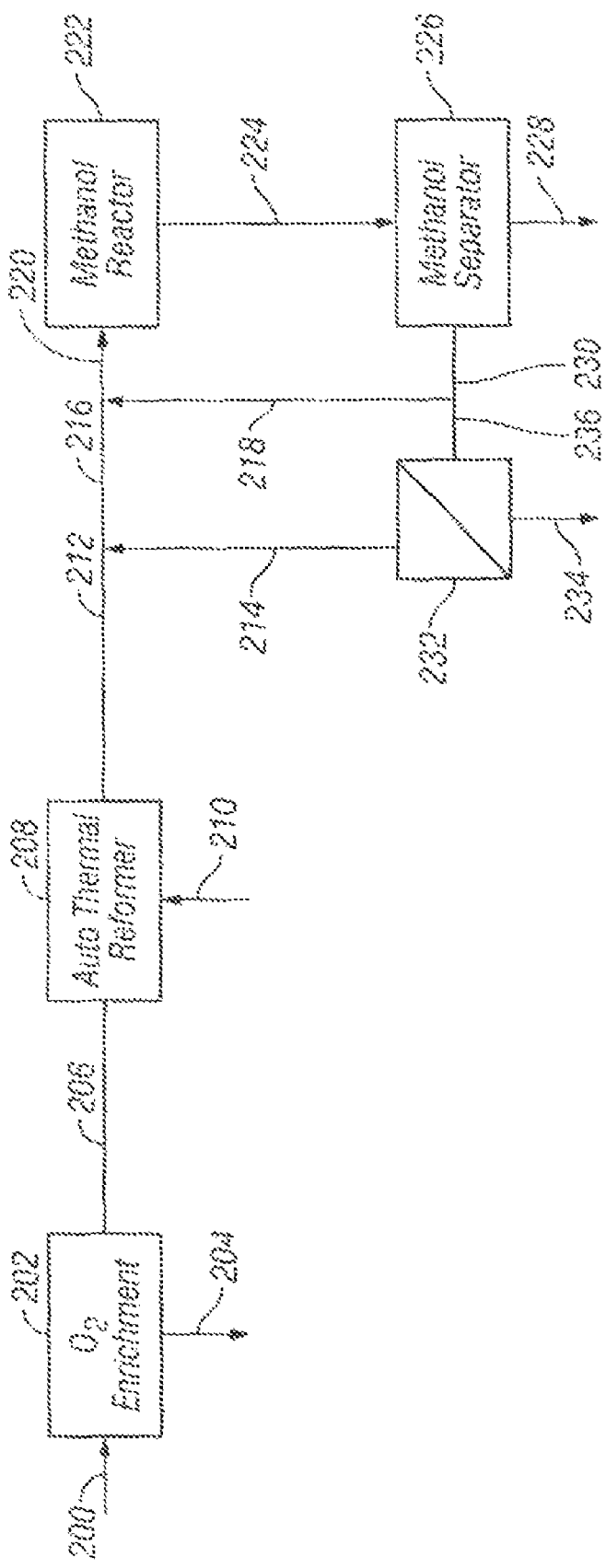
FIG. 2 shows an example of a simple process flow diagram in accordance with the present invention, including the preparation of syn gas from enriched air and natural gas.

FIG. 2 discloses a specific embodiment of the invention. The process begins by providing an air stream 200. Air stream 200 is preferably a compressed air stream having an oxygen content of less than about 22%. Air stream 200 is introduced into a separation system, which yields an enriched oxygen stream 206 comprising at least about 28% oxygen. In one embodiment of the invention, the oxygen content of the air stream is enhanced to between about 35% to about 50%, thereby creating an enhanced oxygen stream. In a specific embodiment, enriched oxygen stream 206 contains at least about 42% oxygen. In another specific embodiment, the enriched oxygen stream 206 has an oxygen content of approximately 70%. In a further embodiment of the invention, the oxygen content of the air stream is enhanced to between about 28% to about 70%, thereby creating an enhanced oxygen stream. The separation system may comprise a semi-permeable membrane, a PSA, or other similar system. Alternatively, the air stream may be enhanced by mixing in oxygen created from a C-ASU unit, or from other known oxygen purification systems, to produce enriched air 206. It should be noted, however, that the synthesis gas stream may be produced by any means in accordance with the invention.

A natural gas stream containing methane 210 is partially oxidized in an ATR using an enhanced oxygen stream 206 to create synthesis gas stream 212. In one embodiment of the invention, the partial oxidizing step creates a synthesis gas stream 212 containing $H_2$, CO, and $CO_2$ in a stoichiometric number of $(H_2-CO_2)/(CO_2+CO)$, which is less than about 1.80; i.e., it is deficient in hydrogen. In a specific embodiment of the invention, the synthesis gas stream 212 is created that has a stoichiometric number of about 1.77. In another specific embodiment of the invention, a synthesis gas 212 is created that has a stoichiometric number of about 1.73. In yet another specific embodiment of the invention, a synthesis gas stream is formed that has a number in the range of about 1.34 and about 1.80.

In a further embodiment of the invention, when hydrogen is extracted from the purge gas stream 236 to form a hydrogen rich stream 214 that is combined with hydrogen poor synthesis gas 212 and recycle gas 218, a reactor feed gas 220 is produced in the reactor 222 with a stoichiometric number between about 2.05 and about 10.

A portion of the reactor feed stream is converted into methanol. The reacted gas 224, which contains methanol, is withdrawn from the reactor vessel 222 and separated into crude liquid methanol product stream 228 and gas stream 230. The gas stream 230 is then split into two streams, the first stream being recycle gas stream 218, which is combined with the makeup gas stream 216 to form the reactor feed gas stream 220. The second portion is a purge gas stream 236. The purge gas stream 236 is separated into two streams, the fuel gas stream 234, which contains $CH_4$, CO, and $CO_2$ and $N_2$, and a hydrogen-rich gas stream 214. The hydrogen-rich stream 214 is then mixed into the synthesis gas stream.

Using the synthesis gas production method disclosed in FIG. 2, the synthesis gas stream will generally comprise approximately 19% nitrogen. In some embodiments, however, the nitrogen content will be in the range of about 6% to about 50%. The present invention permits extremely high levels of inerts to be carried into the methanol loop contrary to 80 years of industry practice. The large quantity of reactants in the significantly increased purge stream are separated from the inert portion of the purge stream and returned to be mixed with the incoming syn gas. This allows a large purge without the loss of valuable reactants. Among other processes, the separation can be done by membranes or PSA.

As discussed above, a method has been previously disclosed wherein methanol is produced by contacting a synthesis gas formed from an oxygen-enriched gas stream for the partial oxidation of natural gas using a methanol loop reactor system. There are key distinctions, however, between this prior art system and the invention described and claimed herein. In the prior art system, a portion of the synthesis gas is not subjected to the methanol production synthesis loop. Rather, the synthesis gas is split into two distinct streams on leaving the ATR. The first stream is diverted to a water gas shift reactor, converting CO to $H_2$, and then through a pressure swing absorber to extract the $H_2$. The $H_2$ that has been distracted joins the second stream and the combined flow is a hydrogen enhanced syn gas with a $N_s$ equal to about 1.85. Since the extraction of the $H_2$ requires the use of additional equipment, one skilled in the art will recognize that the elimination of this extraction step results in a methanol production process that is more efficient and more economical. Additionally, the total methanol yield from the AUS process is lowered by the additional purge required as a result of the additional process equipment.

In a specific embodiment of the present invention, the syn gas comprises about 19 mole % nitrogen and the methanol loop is operated with a high level of $H_2$. The reactor feed gas, therefore, has a stoichiometric number of about 3.3. The excess $H_2$ reacts to maintain the CO at a very low level, i.e., about 3.8 mol %. Thus, there is very little CO in the purge gas. This enables the mols of CO in the fuel gas to be maintained at a value less than 10% of the CO entering the system in the synthesis gas. Similarly, the $H_2$ is separated from the purge stream leaving behind in the fuel gas an amount of $H_2$ that is less than 3.5% of the $H_2$ entering the system in the synthesis gas. The sum of the mols of reactants ($H_2$+CO) leaving the system in the fuel gas is about 5% of that entering the system as syn gas. The $CO_2$ that has not reacted with $H_2$ in the methanol loop will leave the system in the fuel gas. This amounts to about 15% of the $CO_2$ entering the system in the synthesis gas. The retention of $H_2$ in the methanol loop, reacting the CO to low values and rejecting carbon from the system as $CO_2$, will always result in a MUG stoichiometric number greater than 2.05.

A prime benefit of the use of air separation systems is that they allow an alternative to cryogenic oxygen, which significantly reduces the costs associated with the preparation of the synthesis gases. The presence of cryogenic oxygen along with large quantities of methanol creates an extremely hazardous and potentially explosive situation, particularly when there is limited space available, such as on a sea going vessel. The present invention avoids this hazard and allows marine application. All of the embodiments of the invention may be practiced on a seagoing vessel in accordance with the invention. The process can be implemented and completely contained on a ship, barge, or other seagoing vessel. As such, the invention can be brought to natural gas production areas, such as those at offshore production facilities, to convert the abundant natural gas into methanol. The methanol can then be periodically transferred from its seagoing vessel to tankers for transportation to the market. The nominal capacity of the methods of the present invention is approximately 5000 to 15000 metric tons per day ("MTPD").

The $N_s$ the MUG stream can be controlled by the methanol loop design parameters. When the loop pressure is held constant by a back pressure controller in the fuel gas stream or varying the power to the MUG compressor, the inerts will leave the system in the fuel gas stream. In addition, there will be some $H_2$ and CO and a major amount of $CO_2$ leaving in the fuel gas.

In one embodiment of the invention, the MUG comprises $H_2$, CO and $CO_2$ in a ratio of ($H_2$-$CO_2$)/($CO_2$+CO), which is at least about 2.05. In another embodiment of the invention, the MUG comprises $H_2$, CO, and $CO_2$ in a ratio of ($H_2$-$CO_2$)/($CO_2$+CO), which is at least about 2.4. In yet another embodiment of the invention, the MUG comprises $H_2$, CO, and $CO_2$ in a ratio of ($H_2$-$CO_2$)/($CO_2$+CO), which is at least about 3.6.

Although the invention has been described with reference to its various embodiments, from this description, those skilled in the art may appreciate changes and modifications thereto, which do not depart from the scope and spirit of the invention as described herein and claimed hereafter. The following Examples illustrate certain embodiments of the invention, in comparison to the AUS Process. The Examples illustrate specific embodiments of the invention, and is not meant to limit the scope of the invention in any way.

Example I

The impact of the amount of nitrogen in the methanol loop in the methods of the invention on the amount of methanol produced per pound of natural gas was calculated. With reference to Table 1, below, the calculation was performed assuming a concentration of 42% oxygen, 21% oxygen and 70% oxygen in the air stream shown in FIG. 2. The ATR temperature was maintained at 1820° F. The results are shown below in Table 1.

TABLE 1

STOICHIOMETRIC NUMBERS ($N_s$) AND NITROGEN CONTENT ($N_2$) IN THE METHANOL LOOP

| | 42% $O_2$ Air | | 21% $O_2$ Air | | 70% $O_2$ Air | |
| --- | --- | --- | --- | --- | --- | --- |
| | $N_S$ | $N_2$ | $N_S$ | $N_2$ | $N_S$ | $N_2$ |
| ATR out | 1.73 | 16.4 Mol % | 1.62 | 37.6 Mol % | 1.77 | 6.12 Mol % |
| Syn gas | 1.73 | 20.5 | 1.62 | 38.6 | 1.77 | 7.57 |
| MUG | 2.44 | 17.3 | 3.65 | 23.2 | 2.05 | 7.39 |

TABLE 1-continued

STOICHIOMETRIC NUMBERS ($N_s$) AND NITROGEN CONTENT ($N_2$) IN THE METHANOL LOOP

|  | 42% $O_2$ Air | | 21% $O_2$ Air | | 70% $O_2$ Air | |
| --- | --- | --- | --- | --- | --- | --- |
|  | $N_S$ | $N_2$ | $N_S$ | $N_2$ | $N_S$ | $N_2$ |
| RX in | 3.33 | 30.5 | 4.23 | 27.1 | 2.53 | 21.7 |
| RX out | 4.16 | 34.2 | 5.09 | 28.9 | 2.85 | 25.2 |
| Purge gas | 4.24 | 36.9 | 5.06 | 31.1 | 2.94 | 27.8 |
| $H_2$ Rich gas | 7.81 | 8.5 | 6.79 | 7.6 | 5.32 | 6.4 |
| Fuel Gas | 0.27 | 76.3 | 0.59 | 80.2 | 0.12 | 60.0 |
| Mol % ($H_2$ + CO) Lost in Fuel Gas | | 5.5 | | 15.0 | | 2.7 |
| Mol % $CO_2$ Lost in Fuel Gas | | 15.7 | | 50.6 | | 10.1 |
| Methanol/ Natural Gas Pound/pound | | 1.57 | | 1.37 | | 1.61 |

The results show the level of oxygen enrichment has an insignificant effect on the stoichiometric number of the effluent from the ATR. It is less than 1.77. Table 1 demonstrates that the process shown in FIG. 1 will produce a MUG with stoichiometric number greater than about 2.05 when supplied with syn gas containing nitrogen greater than about 7.6 mol %. When the nitrogen is discharged from the methanol loop, excess carbon in the form of $CO_2$ is discharged along with it leaving the hydrogen in surplus in the methanol loop.

The methanol made per pound of natural gas increased 15% when the oxygen concentration increased from 21% to 42%. However, the increase in methanol was only 2.5% when the oxygen increased from 42% to 70%.

Example II

Figure 3:
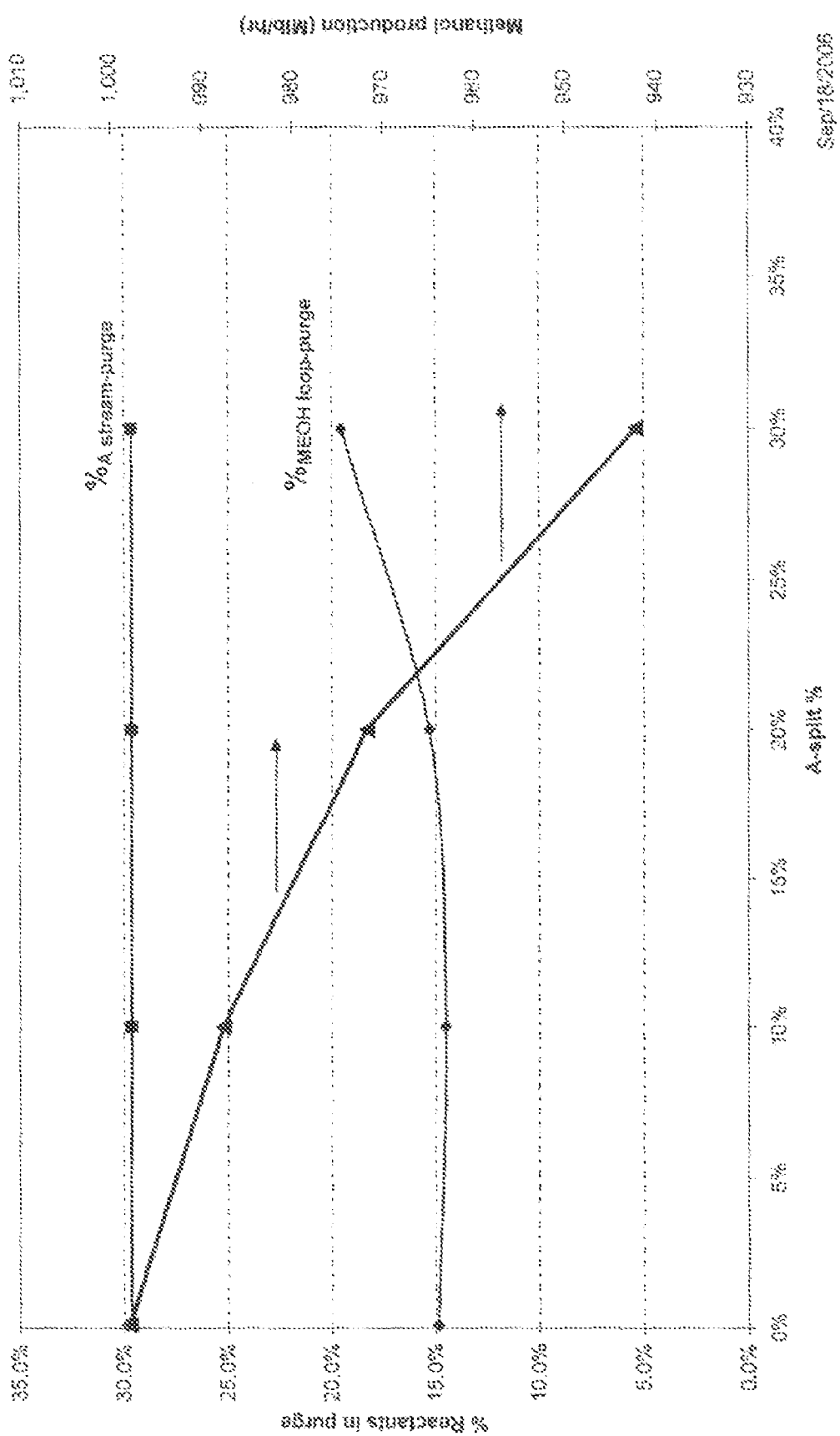

With reference to FIGS. 3 and 4 the methanol production process described in the AUS Process was used to produce methanol using an Aspen process simulator. Aspen standard data was used, including equilibrium constants out of the ATR and the methanol reactors (35° F. approach), as well as membrane and PSA efficiencies.

Parameters for the study were from the Starchem Plantship analysis performed by Lurgi. The parameters dictated the natural gas and air flow rates, steam/carbon, pressures, cooling water temperatures, etc. A water quench to 500° F. out of the ATR was used when flow was into path A. Quench is necessary to avoid metal dusting and provide steam for the water gas shift. For calculations with zero flow into path A, also known as the $H_2$ extraction stream, no quench was used.

Two sessions were performed. The first involved varying the percentage of flow into path A in 10% increments. It was found that any amount of flow into path A resulted in a decreasing methanol yield as the flow increased. The second session involved increasing the efficiency of $H_2$ separation in path A from 70% to 85%.

The results from the second session are shown in FIG. 4. The syn gas, after combining with stream A, had a stoichiometric number of 1.85 and the MUG stoichiometric number was 2.8. The production of methanol decreased as flow was increased into path A. As illustrated, one embodiment of the processes of the invention, i.e. zero flow into path A, produced more methanol than the AUS Process.

The total amount of inerts that must be purged from the process is the same in both the AUS Process and the methods of the invention describe herein. The purge from path A, however, always has a higher concentration of reactants ($H_2$ + CO) than the purge from the methanol loop. Thus, more reactants that could be converted to methanol are lost when there is flow into path A. When path A is utilized, methanol is produced at a rate of 997,948 lb/hr. As the amount of synthesis gas diverted to path A is increased, however, the amount of methanol produced decreases. When path A diverts 30% of the synthesis gas, methanol is produced at a rate of only 942,306 lb/hr., which is an at least 5% decrease.

The method of control of the invention described and claimed herein renders the AUS Process split of synthesis gas into two streams totally unnecessary and, in fact, harmful to the methanol yield. One stream in AUS Process has the hydrogen content enhanced by water gas shift and rejects nitrogen and $CO_2$. In the present methods of the invention, the water gas shift occurs in the methanol reactor and the $N_2$ and $CO_2$ rejection are performed at a much lower cost and at the same time, more of the reactants are preserved to make additional methanol.

Although the invention has been described with reference to its various embodiments, from this description, those skilled in the art will understand that certain changes and modifications to the various embodiments of the invention, which do not depart from the scope and spirit of the invention, are nevertheless within the scope of the invention.

I claim:

1. A process for producing methanol, comprising the steps of:
   providing an air stream comprising oxygen;
   providing a natural gas stream comprising methane;
   partially oxidizing the natural gas stream in an autothermal reformer using the air stream to create a synthesis gas stream comprising $H_2$, CO, and $CO_2$ and $N_2$;
   combining the synthesis gas stream with a hydrogen-rich gas stream to form a makeup gas stream;
   combining the makeup gas stream with a recycle gas stream to produce a reactor feed stream;
   introducing the reactor feed stream into a reactor system containing a methanol conversion catalyst; wherein a portion of the reactor feed stream is converted to methanol;
   withdrawing a reacted gas stream from the reactor system;
   separating the reacted gas stream into a crude methanol product stream and a gas stream;
   splitting the gas stream into a recycle gas stream and a purge gas stream;
   combining the recycle gas stream with the makeup gas stream to form the reactor feed stream;

separating the purge gas stream into a fuel gas stream comprising $CH_4$, and $N_2$ and a hydrogen-rich stream comprising $H_2$; and mixing the hydrogen-rich stream into the synthesis gas stream.

2. The process of claim 1 wherein said air stream has an oxygen content less than 22%, and said process further includes the step of enhancing the oxygen content of the air stream to between about 28% and 94% oxygen.

3. The process of claim 2 wherein the oxygen content of the air stream is enhanced to between about 28% and 70%.

4. The process of claim 2 wherein the oxygen content of the air stream is enhanced to between about 35% and 50%.

5. The process of claim 1 wherein the synthesis gas stream comprises at least about 6 mole % $N_2$.

6. The process of claim 1 wherein the synthesis gas stream comprises at least about 8 mole % $N_2$.

7. The process of claim 1 wherein the synthesis gas stream comprises at least about 20 mole % $N_2$.

8. The process of claim 1 wherein the synthesis gas stream comprises at least about 35 mole % $N_2$.

9. The process of claim 1 wherein the natural gas is converted to methanol on a seagoing vessel.

10. The process of claim 1 wherein the synthesis gas stream comprises $H_2$, CO, and $CO_2$ in a ratio of $(H_2-CO_2)/(CO_2+CO)$, which is less than about 1.77.

11. The process of claim 1 wherein the synthesis gas stream comprises $H_2$, CO, and $CO_2$ in a ratio of $(H_2-CO_2)/(CO_2+CO)$, which is less than about 1.73.

12. The process of claim 1 wherein the synthesis gas stream comprises $H_2$, CO, and $CO_2$ in a ratio of $(H_2-CO_2)/(CO_2+CO)$, which is between about 1.34 and about 1.80.

13. The process of claim 1 wherein the makeup gas stream comprises $H_2$, CO, and $CO_2$ in a ratio of $(H_2-CO_2)/(CO_2+CO)$, which is at least about 2.05.

14. The process of claim 1 wherein the makeup gas stream comprises $H_2$, CO, and $CO_2$ in a ratio of $(H_2-CO_2)/(CO_2+CO)$, which is at least about 2.4.

15. The process of claim 1 wherein the makeup gas stream comprises $H_2$, CO, and $CO_2$ in a ratio of $(H_2-CO_2)/(CO_2+CO)$, which is at least about 3.6.

* * * * *